United States Patent [19]
Watson

[11] Patent Number: 5,447,498
[45] Date of Patent: Sep. 5, 1995

[54] MESH LUMBAR SUPPORT BELT

[76] Inventor: George W. Watson, 18250 Willamette Dr., West Linn, Oreg. 97068

[21] Appl. No.: 236,891

[22] Filed: May 2, 1994

[51] Int. Cl.⁶ .............................................. A61F 5/00
[52] U.S. Cl. ................................... 602/19; 128/99.1
[58] Field of Search ............... 428/225, 246, 257–259, 428/296; 602/19; 128/99.1, 100.1, 101.1

[56] References Cited

U.S. PATENT DOCUMENTS

| | | |
|---|---|---|
| 1,075,348 | 10/1913 | Fritsch . |
| 2,541,487 | 2/1951 | Triplett . |
| 2,843,116 | 7/1958 | Grannan . |
| 3,970,079 | 7/1976 | Gaylord, Jr. . |
| 4,143,197 | 3/1979 | Jasionowicz et al. . |
| 4,473,432 | 9/1984 | Leader et al. . |
| 4,474,585 | 10/1984 | Gruber . |
| 4,501,782 | 2/1985 | Weatherly et al. . |
| 4,804,351 | 2/1989 | Raml et al. . |
| 4,900,613 | 2/1990 | Green ........................ 428/259 X |
| 5,070,866 | 10/1991 | Alexander et al. . |
| 5,192,601 | 3/1993 | Neisler . |
| 5,205,815 | 4/1993 | Saunders ........................ 602/19 |
| 5,292,328 | 3/1994 | Hain et al. . |

*Primary Examiner*—Linda C. M. Dvorak
*Attorney, Agent, or Firm*—Chernoff, Vilhauer, McClung & Stenzel

[57] ABSTRACT

An elongate semiflexible woven lumbar support belt has a wide central support portion and a pair of interconnectable opposite end portions which are significantly narrower than the central support portion. The central support portion is formed from a webbing having a plurality of warp strands interwoven with a plurality of weft strands. The warp and weft strands, respectively, are fixedly attached to each other at angular junctions such that the stiffness of the webbing is greater than if the strands were not fixedly attached to each other at the angular junctions. The warp strands are spaced apart from each other and the weft strands likewise are spaced apart from each other to provide ventilation through the webbing.

7 Claims, 1 Drawing Sheet

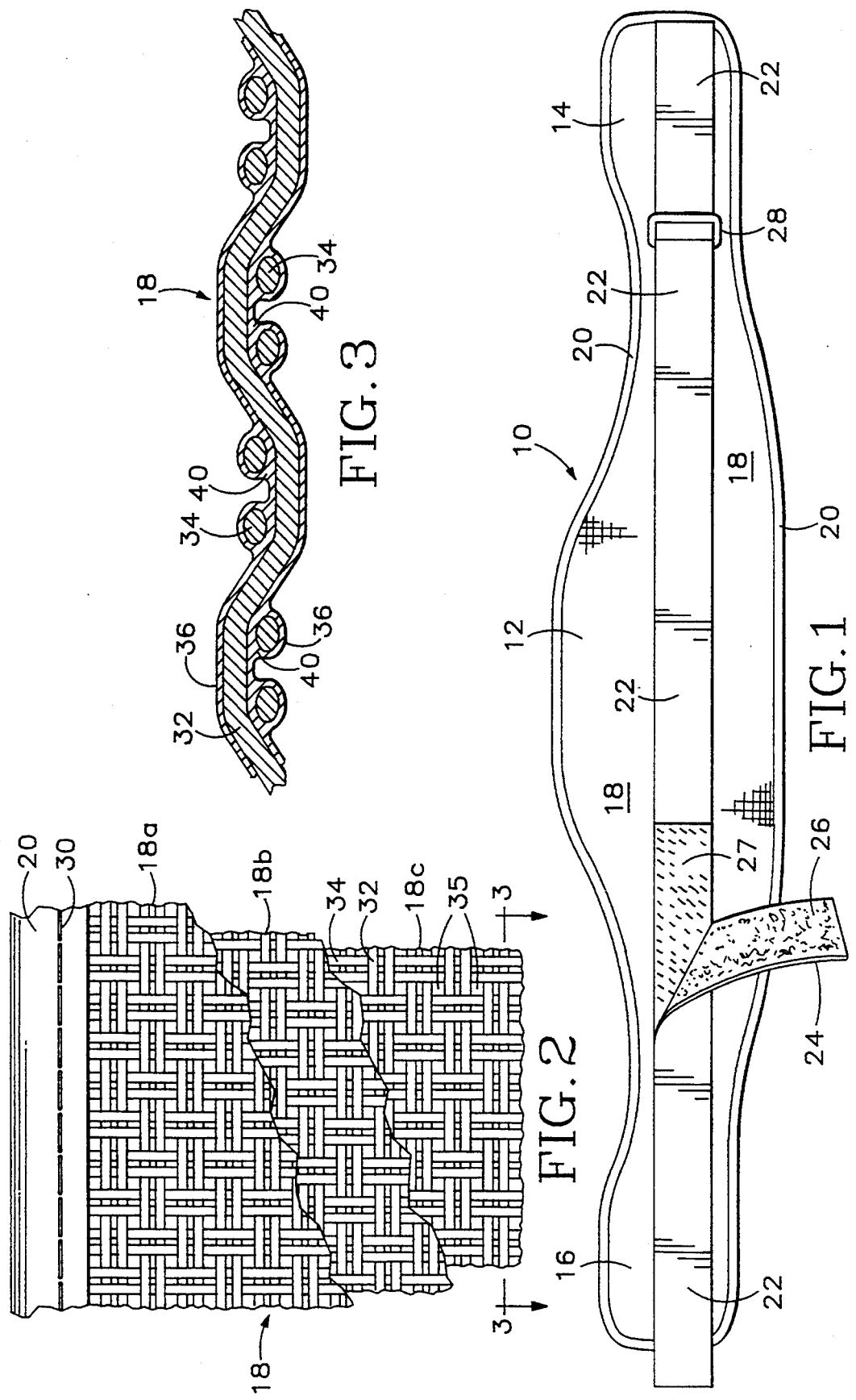

MESH LUMBAR SUPPORT BELT

BACKGROUND OF INVENTION

This invention relates to an improvement in the design of lumbar support belts.

Participation in various occupations and sporting events such as manufacturing, moving and storage, heavy equipment operation, construction, weightlifting, motorcross and the like often places a considerable strain on the lower back. Efforts to alleviate back strain problems have been satisfactorily achieved through the use of lumbar (back) support belts of heavy, tightly woven fabric or traditional stiff leather. Such belts are tightened around the waist of the user with a wide central support portion abutting the lower back prior to engaging in activities where conditions are conducive to possible lower back strain. Such belts are commercially available in various widths and thicknesses to provide a suitable level of rigidity for supporting the user's lower back in his chosen activity.

Although current lumbar support belts are adequately designed to support the lower back, they do not provide a high degree of comfort. The user's skin covered by the wide central support portion of the belt often becomes hot, sweaty, and irritated during activity, and the skin at the edges of the belt may become chafed due to the belt's stiffness, all of which result in substantial discomfort to the user. Attempting to alleviate these drawbacks, some lumbar support belts have been provided with numerous holes in the central support portion for ventilation to reduce the heat and sweat developed during activity. However such ventilation is insufficient to provide the cooling required. If a greater density of holes were provided to increase the ventilation, the belts would lack sufficient structural stiffness to provide adequate support for the lower back.

Alexander et al. U.S. Pat. No. 5,070,866 discloses a semi-flexible back support belt with selective rigidity control. The belt comprises tightly-woven webbing formed of multiple layers or plies which are tied together by longitudinally extending binder yarns. The binder yarns provide a belt-rigidizing hinge arrangement within the webbing responsive to the application of longitudinally applied tensile loading on the belt. The necessity of a tight weave pattern prevents the belt from providing sufficient ventilation to minimize the sweat and heat created during its use. In order to provide selective rigidity control, the yarns cannot be fixed to each other but rather must be relatively movable with variations in the applied tension to allow for the hinged arrangement.

Gaylord U.S. Pat. No. 3,970,079 discloses a support binder utilizing an elastic woven textile fabric which has no ventilation capacity nor any stiffness apart from its plastic joints.

Raml U.S. Pat. No. 4,804,351 discloses a post-operative brassiere with an open-weave fabric that has some ventilation capacity. However, the open-weave fabric is a stretchable material which does not have the rigidity nor stiffness required for use as a back support belt.

To provide lumbar support, designers have also relied on a variety of schemes such as those shown in the following other U.S. Pat. Nos. 2,843,116; 2,541,487; 1,075,348.

SUMMARY OF THE INVENTION

The present invention overcomes the foregoing drawbacks of the prior art by providing an elongate semi-flexible woven lumbar support belt having a wide central support portion formed of a webbing having loosely woven, spaced-apart warp and weft strands fixedly attached to each other at their angular crossing junctions such that the stiffness of the webbing is greater than if the strands were not fixedly attached to each other. The loose, spaced-apart strands of the webbing provide a high degree of ventilation for reducing the heating and sweating of the skin covered by the wide central support portion of the belt, while the fixed angular attachment of the spaced weft and warp strands to each other at their angular junctions compatibly provides the necessary stiffness for adequate lumbar support over a sufficient area.

The stiffness provided by the lumbar support belt does not, however, produce stiff edges leading to discomfort due to chafing. Chafing is preferably minimized by using multiple overlying layers of webbing slidably movable relative to each other, rather than a single thick layer of webbing. Such multiple layers of webbing have a greater tendency to bend at or near the edges which reduces chafing, and their relative slidability also maximizes the desired ventilation characteristics of the webbing. Moreover, such relative slidability makes the webbing form-fitting and moldable to the body shape for maximum support.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

FIG. 1 is an exemplary embodiment of a lumbar support belt of the present invention.

FIG. 2 is an enlarged, partial cut-away view of the lumbar support belt of FIG. 1 showing three layers of webbing.

FIG. 3 is an enlarged cross-sectional view taken along line 3—3 of FIG. 2.

DESCRIPTION OF THE PREFERRED EMBODIMENT

Referring to FIG. 1, an exemplary embodiment of the lumbar support belt 10 has a wide central support portion 12 and a pair of interconnectable opposite end portions 14 and 16 which are significantly narrower than the central support portion 12. The belt's length is preferably slightly more than required to encompass the waist of the user so that the belt may tightly fasten to the body of the user with the opposite end portions 14 and 16 overlapping each other. The width of the central support portion 12 may vary for the user's particular activity and the amount of support necessary.

The body of the belt 10 is comprised of one or more layers of webbing 18 to be described in detail hereafter. Along the edge of the webbing 18 is a binding material 20 that is stitched to the webbing 18 with a suitable thread 30 (see FIG. 2), such as nylon or polyester. The binding material 20 provides a rounded cushion between the edge of the webbing 18 and the user's skin to aid in reducing chafing, while the thread 30 secures multiple layers of webbing 18a, 18b, 18c (FIG. 2) together near the edges so that the layers are fastened to, and yet are slidably movable with respect to, each other as the webbing bends. Thus, the ventilation characteristics, flexible comfort and form-fitting support of the belt are not impeded by any bonding of the layers to one another.

The belt 10 has a strap 22 constructed of a tightly woven webbing (or other suitable material) securely stitched at the strap's outer edges to the webbing 18. The strap 22 has a long end portion 24 having mating strips of Velcro TM material 26 and 27. The belt is worn by separating the strips 26 and 27 and placing the belt 10 around the user's waist, after which the end portion 24 is guided through the buckle 28, cinched around the user's waist to the desired tension, and fastened by pressing the strips 26 and 27 together. Alternatively, any other conventional type of belt-securing method could be used.

Referring to FIG. 2, a partial cut-away view of the belt is shown with three layers of webbing 18a, 18b, and 18c held together by the binding material 20 and thread 30. Although three layers of webbing 18a, 18b, 18c are shown, any number of layers of webbing 18 could be used depending upon the overall stiffness desired. An additional partial layer of webbing (not shown) is also preferably added to the area underlying the buckle 28 for reinforcement.

A layer of webbing 18 is constructed from a plurality of interwoven, mutually perpendicular warp and weft strands 32, 34, respectively, to form a mesh. The warp strands 32 are spaced apart to provide for gaps between them, as is the case also with respect to the weft strands 34. By so spacing the respective warp and weft strands, four-sided apertures such as 35 are defined which permit air to circulate to the skin of the user uniformly over the area covered by the belt 10. Preferably, the warp and weft strands are grouped as respective pairs of strands to produce a basketweave as shown, rather than a plain weave. The basketweave is preferred to provide larger apertures 35 in the webbing for a given webbing weight compared to a plain weave. Although the warp and weft strands are shown as being oriented parallel and transverse, respectively, to the length of the belt 10, there is no requirement that they necessarily be aligned in those directions, nor that they necessarily cross each other at 90° angles.

Each of the warp 32 and weft 34 strands is preferably of 1800 D (denier) polyester multifilament yarn covered by a moisture-impervious flexible plastic coating 36 such as PVC having a thickness of about 0,030 inch. Polyester yarn in the range of 1000 to 2600 denier would be satisfactory, as well as coating diameters in the range of 0,028 to 0,040 inch. Preferably, conventional anti-static and anti-inflammable agents are added to the PVC for use in those industries where such hazards exist. The PVC coating is applied to the yarn as a liquid PVC plastisol (using a die wipe process) which is then cured in a heated oven. Two coats of plastisol are applied, but additional coats could be applied if a greater thickness is desired. There is some impregnation of the polyester filaments by the coating so that a border between the core yarn and coating is not clearly defined when viewed in cross section. This impregnation serves to provide a greater stiffening effect to the yarn than if such impregnation did not occur. Some added stiffness is also imparted to the yarn owing to the fact that the plastisol is cured by external application of heat which volatilizes a small amount of plasticizer, producing a slight case-hardening effect on the PVC surface. Preferably, 13 strands of warp and 13 strands of weft intersect each other per square inch of webbing. Despite the foregoing preferred specifications for the webbing, it should be understood that other suitable materials, sizes and spacings may be used if desired and are within the scope of the present invention.

Despite the spaced, loose weave of the warp and weft strands in the webbing to create the desired ventilation, the webbing nevertheless has the stiffness of a much tighter weave material. With reference to FIG. 3, this is because the warp and weft strands are fixedly attached to each other at the angular junctions where they cross each other to increase the stiffness. The fixed attachment of the warp and weft strands to each other at their respective angular junctions is accomplished by heat-finishing the webbing after it has been woven by passing it through an oven using a tenter frame and applying heat to fuse the plastic coatings 36 to each other at their angular junctions 40 which, after cooling, forms a fixed, rigid bond between the warp and weft strands at the angular junctions 40. The temperature in the tenter frame oven is 350°–425° F., with 400° F. being preferred. The oven residence time for the webbing is 30 to 75 seconds, with 50–60 seconds being preferred. Bonding of the coated strands takes place at the angular junctions in the presence of the softened vinyl and yarn tension forces generated by the heat shrinkage propensity of the polyester.

A single layer of webbing 18 could be manufactured using thick weft and warp strands to provide the necessary stiffness for lumbar support. However, it is preferable to use thinner weft and warp strands to create a thinner layer of webbing 18. Then, using multiple layers of the thinner webbing 18 as shown in FIG. 2, the necessary stiffness can be achieved. The multiple layers of thinner webbing 18 have a greater tendency to bend at or near the edges and reduce chafing. Moreover, the slidability of the layers relative to each other also helps to maximize the desirable ventilation characteristics of the webbing, and provide form-fitting support moldable to the body shape.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. An elongate semiflexible woven lumbar support belt having a wide central support portion and a pair of interconnectable opposite end portions which are significantly narrower than said central support portion, at least said central support portion being formed of a webbing having a plurality of warp strands interwoven with a plurality of weft strands, said warp and weft strands, respectively, being fixedly attached to each other at angular junctions such that the stiffness of said webbing is greater than if said strands were not fixedly attached to each other at said angular junctions, said warp strands being spaced apart from each other and said weft strands likewise being spaced apart from each other to provide ventilation through said webbing.

2. The support belt of claim 1, further comprising multiple layers of said webbing positioned in overlying relationship to each other in said central support portion.

3. The support belt of claim 2 wherein the respective warp and weft strands of at least one of said multiple layers of said webbing are slidably movable relative to the respective warp and weft strands of another of said layers.

4. The support belt of claim 1 wherein said warp and weft strands are fused to each other at said angular junctions.

5. An elongate semiflexible woven lumbar support belt having a wide central support portion and a pair of interconnectable opposite end portions which are significantly narrower than said central support portion, at least said central support portion being formed of a webbing having a plurality of warp strands interwoven with a plurality of weft strands, said warp and weft strands, respectively, being fixedly attached to each other at angular junctions such that the stiffness of said webbing is greater than if said strands were not fixedly attached to each other at said angular junctions, said warp strands being spaced apart from each other and said weft strands likewise being spaced apart from each other to provide ventilation through said webbing, said central support portion comprising multiple layers of said webbing having an overlap area where said layers are positioned in overlying relationship to each other, said layers being free of any interweaving with each other over at least a major portion of said overlap area.

6. The support belt of claim 5 wherein the respective warp and weft strands of at least one of said multiple layers of said webbing are slidably movable relative to the respective warp and weft strands of another of said layers.

7. The support belt of claim 5 wherein said warp and weft strands of each of said multiple layers are fused to each other at said angular junctions.

* * * * *

UNITED STATES PATENT AND TRADEMARK OFFICE
CERTIFICATE OF CORRECTION

PATENT NO. : 5,447,498

DATED : September 5, 1995

INVENTOR(S) : George W. Watson

It is certified that error appears in the above-indentified patent and that said Letters Patent is hereby corrected as shown below:

Col. 3, line 49   Change "0,030" to --0.030--.

Col. 3, line 52   Change "0,028" and "0,040" to --0.028-- and --0.040--.

Signed and Sealed this

Twenty-sixth Day of December, 1995

Attest:

BRUCE LEHMAN

Attesting Officer        Commissioner of Patents and Trademarks